United States Patent
Murray et al.

(10) Patent No.: US 6,566,565 B1
(45) Date of Patent: May 20, 2003

(54) PROCESS FOR PREPARATION OF SELECTIVELY BRANCHED DETERGENT PRODUCTS

(75) Inventors: Brendan Dermot Murray, Houston, TX (US); David Michael Singleton, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/566,460

(22) Filed: May 8, 2000

(51) Int. Cl.[7] ............... C07C 27/20; C07C 27/22; C07C 27/24; C07C 29/15
(52) U.S. Cl. ............................................. 568/909
(58) Field of Search ..................... 568/909; 585/820

(56) References Cited

U.S. PATENT DOCUMENTS

| | | | |
|---|---|---|---|
| 3,674,886 A | 7/1972 | Komatsu et al. | |
| 3,676,523 A | 7/1972 | Mason | 260/683.15 D |
| 3,686,351 A | 8/1972 | Mason | 260/683.15 D |
| 3,737,475 A | 6/1973 | Mason | 260/683.15 D |
| 3,770,619 A | 11/1973 | Derrien et al. | |
| 3,825,615 A | 7/1974 | Lutz | 260/683.15 D |
| 4,020,121 A | 4/1977 | Kister et al. | 260/683.15 D |
| 4,076,842 A | 2/1978 | Plank et al. | 423/328 |
| 4,351,980 A * | 9/1982 | Reusser et al. | 585/820 |
| 4,551,443 A | 11/1985 | Hudson | |
| 4,717,785 A * | 1/1988 | Paxon | 585/823 |
| 5,072,057 A | 12/1991 | Oswald et al. | |
| 5,112,519 A | 5/1992 | Giacobbe et al. | 252/174.21 |
| 5,376,393 A * | 12/1994 | Nardelli et al. | 426/271 |
| 5,387,439 A | 2/1995 | Roberts | |
| 5,510,306 A | 4/1996 | Murray | 502/64 |
| 5,780,694 A * | 7/1998 | Singleton | 568/909 |
| 5,849,960 A * | 12/1998 | Singleton et al. | 568/909 |
| 5,994,591 A | 11/1999 | Arnoldy et al. | 568/454 |
| 6,084,140 A | 7/2000 | Kitamura et al. | |

FOREIGN PATENT DOCUMENTS

| | | | |
|---|---|---|---|
| EP | 0903333 A1 | 7/1998 | C07C/45/50 |

OTHER PUBLICATIONS

U.S. patent application Ser. No. 10/216,522, Murray et al., filed Aug. 9, 2002.
U.S. patent application Ser. No. 09/566,461, Murray et al., filed May. 8, 2000.
U.S. patent application Ser. No. 09/566,462, Himelfarb et al., filed May, 8, 2000.
U.S. patent application Ser. No. 09/566,463, Murray et al., filed May, 8, 2000.
Verfarhren Zur Katalytishen Oligomerisierung Von Monoolefinen Research Disclosure, Kenneth Mason Publications, Hampshire, GB, No. 415, Nov. 1998, pp. 1445–1451, XP000824939.

* cited by examiner

*Primary Examiner*—Samuel Barts
*Assistant Examiner*—Elvis O. Price

(57) ABSTRACT

The invention pertains to a process of making selectively branched alcohol compositions by oligomerizing a lower olefin feed. The lower olefin feed preferably comprises linear olefins having at least three carbon atoms.

114 Claims, No Drawings

PROCESS FOR PREPARATION OF SELECTIVELY BRANCHED DETERGENT PRODUCTS

FIELD OF THE INVENTION

The invention relates to a process for preparing olefins used in forming surfactants. Specifically, the invention relates to the formation of selectively branched olefins which are converted to biodegradable, selectively branched alcohols.

BACKGROUND OF THE INVENTION

Alcohols of long chain olefins having about 6 to 36 carbon atoms have considerable commercial importance in a variety of applications, including detergents, soaps, surfactants, and freeze point depressants in lubricating oils. These alcohols are produced by a number of commercial processes, such as by oxo or hydroformylation of long chain olefins. Typical commercially available long chain alcohols are the NEODOL® alcohols available from Shell Chemical Company, the EXXAL® alcohols available from Exxon Chemical Company, and the LIAL® alcohols available from Enichem.

In the manufacture of the NEODOL® alcohols, a predominantly linear olefin feed is subjected to hydroformylation by reacting carbon monoxide and hydrogen onto the olefin in the presence of an oxo catalyst to form an alcohol. Over 80% of the alcohol molecules in the resulting alcohol are linear primary alcohols. Of the branched primary alcohols in the composition, most, if not all of the branching is on the $C_2$ carbon atom relative to the hydroxyl bearing carbon atom. These alcohols subsequently can be converted to anionic or nonionic detergents or general surfactants by sulfonation or ethoxylation of the alcohol, or by conversion of the alcohol to an alcohol-ethoxysulfate.

The NEODOL® alcohols are commercially successful intermediates to the production of detergents. One reason for this success undoubtedly is that the NEODOL® alcohols are economically produced with high yields of linear alcohols. The sulfonates of linear alcohols are more biodegradable than the sulfonates of highly branched long chain alcohols. Since detergents and soaps used by consumers for washing ultimately are released into the environment, the need for surfactants or detergents with acceptable biodegradability is well recognized.

The highly linear NEODOL® alcohols have the advantage of a high level of biodegradability; however, the high degree of linearity of these alcohols also increases their hydrophobicity, thereby decreasing their cold water solubility/detergency. Thus, there is a need for an alcohol composition having both increased biodegradability and increased solubility.

Alcohols that have been found to meet both the biodegradability and the solubility government standards are branched primary alcohols and their sulfate derivatives: having about 8 to about 36 carbon atoms; having an average number of branches per molecular chain of at least 0.7; having less than 0.5 atom % of quaternary carbon atoms; and, having at least methyl and ethyl branching. These alcohols, as well as a method for preparing them, are described in U.S. Pat. No. 5,849,960, incorporated herein by reference. The method basically involves contacting a feed comprising linear olefins having 7 to 35 carbon atoms with a skeletal isomerization catalyst, and converting the resulting skeletally isomerized olefin to a saturated branched primary alcohol, preferably by hydroformylation. Methods capable of producing similar compounds with greater operating efficiency are always desirable.

SUMMARY OF THE INVENTION

The present invention provides a process for making a selectively branched alcohol composition. The process comprises contacting an oligomerization catalyst under oligomerization conditions with an olefin feed comprising linear olefins having at least 3 carbon atoms. The oligomerization catalyst is effective to oligomerize the linear olefins to produce selectively branched olefins having up to about 36 carbon atoms. One or both of the olefins selected from the group consisting of the selectively branched olefins and the olefin feed comprise a concentration of an impurity selected from the group consisting of dienes and phosphorous containing compounds. The concentration of the impurity is reduced in a material selected from the group consisting of the olefin feed and the selectively branched olefins. The selectively branched olefins are converted to the selectively branched alcohol composition.

DETAILED DESCRIPTION OF THE INVENTION

The present invention relates to a process for oligomerizing lower olefins having at least 3 carbon atoms, preferably from about 3 to about 18 carbon atoms, most preferably from about 6 to about 10 carbon atoms, into selectively branched olefins having from about 6 to about 36 carbon atoms, preferably from about 11 to about 20 carbon atoms, and most preferably from about 14 to about 18 carbon atoms. The selectively branched olefins are hydroformylated and converted to selectively branched alcohols. An oligomerization catalyst is used to oligomerize the olefins, thereby increasing carbon number and selective branching. The selectively branched alcohols preferably are used to prepare biodegradable surfactants for use in detergent formulations.

The process of oligomerization to form selectively branched olefins is defined to mean subjecting olefins having fewer carbon atoms to conditions that form longer chains having more carbon atoms.

The resulting selectively branched olefins typically contain at least some dienes, which tend to poison and reduce the overall effectiveness of the hydroformylation catalyst. In order to prevent this poisoning, the dienes present in the selectively branched olefins preferably are removed prior to hydroformylation. The selectively branched olefins are hydroformylated to form a saturated alcohol which may be sulfonated or ethoxylated. The dienes also be may removed from the lower olefins prior to oligomerization, in order to prevent potential poisoning of the oligomerization catalyst.

Depending upon the catalyst used to make the lower olefins, phosphorus may be present in the lower olefin feed. Basic phosphorus compounds tend to reduce the effectiveness of the oligomerization catalyst and it is therefore desirable to remove the phosphorus from the lower olefin feed prior to oligomerization.

Olefin Feed

Suitable olefins used in the olefin feed for oligomerization are "lower olefins" defined herein as mono-olefins having at least 3 carbon atoms, preferably having from about 3 to about 18 carbon atoms, and most preferably having from about 6 to about 10 carbon atoms. In general, the olefins in the lower olefin feed are predominately linear. While the lower olefin feed may contain some selectively branched olefins, the lower olefin feed preferably contains greater than about 50 wt. %, more preferably greater than about 70 wt. %, and most preferably greater than about 80 wt. % or more of linear lower olefin molecules.

Lower olefins are available from a wide variety of sources. The lower olefin feed may not consist of 100% olefins within the specified carbon number range. The lower olefin feed may contain olefins of other carbon number or carbon structure, diolefins, paraffins, and other impurities. The location of the double bond is not limited. The lower olefin feed composition may comprise alpha-olefins, internal olefins, or a mixture thereof.

Commercial olefin products manufactured by ethylene oligomerization are marketed in the United States by Shell Chemical Company under the trademark NEODENE and by Ethyl Corporation as ALPHA-OLEFINS. Specific procedures for preparing suitable lower olefin feeds from ethylene are described in U.S. Pat. Nos. 3,676,523, 3,686,351, 3,737, 475, 3,825,615 and 4,020,121, the teachings of which are incorporated herein by reference.

Oligomerization Catalyst, Conditions and Product

The catalyst used to treat the lower linear olefins is effective to oligomerize a lower olefin composition into an olefin composition having an average number of branches per molecule chain of at least 0.7. A preferred catalyst contains a medium pore zeolite having at least one channel with a crystallographic free channel diameter from about 4.2 Å to about 7 Å, measured at room temperature, with essentially no channel present which has a free channel diameter which is greater than 7 Å. One such suitable medium pore size zeolite is ZSM-23, disclosed in U.S. Pat. No. 5,112,519 which is incorporated by reference herein. ZSM-23 crystalline structure is readily recognized by its X-ray diffraction pattern, which is described in U.S. Pat. No. 4,076,842 (Rubin, et al), incorporated by reference.

Preferred catalysts for use in the present invention are ferrierite molecular sieves (also known as ZSM-35) particularly including but not necessarily limited to those described in U.S. Pat. No. 5,510,306 which is incorporated by reference herein. Using these ferrierite catalysts, the oligomerization of lower olefins is carried out at partial pressures that range from about 1 to about 400 atm, preferably about 10 atm to about 200 atm and at a temperatures of from about 100° C. to about 400° C., preferably from about 150° C. to about 300° C. The reaction preferably is conducted in the liquid phase. These conditions also allow skeletal isomerization of the resulting oligomers such that the desired range of selectively branched olefins are formed.

Additional suitable "oligomerization catalysts" include but are not necessarily limited to the homogenous dimerization catalysts disclosed in U.S. Pat. No. 5,780,694 (the '694 patent) which is incorporated by reference herein. As used herein the phrase "oligomerization conditions" is defined to include suitable conditions for dimerization using such homogeneous dimerization catalysts. Such conditions include temperatures of from about −10° C. to about 100° C., preferably from about 20° C. to about 50° C. for about ½ to about 8 hours, preferably about 1 to about 5 hours, using an olefin to catalyst mole ratio of about 200 to 20,000, preferably 1,000 to 110,000 moles of olefin per mole of catalyst. The dimerization is preferably conducted as a liquid phase reaction using pressures of from about 0 to about 3 atmospheres, preferably about 1 to about 2 atmospheres. Where the dimerization is conducted as a batch process, the catalyst can be conveniently prepared in situ in the reactor. The dimerization can also be conducted as a continuous, semi-batch or multi-step process. It should be appreciated that where typical or preferred process conditions such as temperatures, times, and catalyst ratios have been given, other process conditions also may be used. Optimum process conditions may vary with the particular reactants, catalysts, or solvents used, but can be determined by routine optimization procedures.

Preferred homogenous dimerization catalysts comprise a combination of a nickel carboxylate or a nickel chelate, with an alkyl aluminum halide or an alkyl aluminum alkoxide, respectively. A suitable Al/Ni mole ratio is from about 1.0 to about 20.0. The nickel and aluminum compounds used are described in the '694 patent. The catalyst optionally also may contain a small amount of water which has the effect of increasing the rate of the catalytic dimerization. Generally, the amount of water employed will be an amount sufficient to increase the rate of the catalytic dimerization.

The selectively branched olefins have an average number of branches of from about 0.7 to about 2.0 per molecule. Suitable branches have from about 1 to about 3 carbon atoms. Preferably a majority of the selectively branched olefins are mono-branched, meaning they contain a single hydrocarbon branch, preferably having from about 1 to about 3 carbon atoms, most preferably one carbon atom.

Phosphorus Removal

The presence of undesirable phosphorus compounds in the lower olefin feed tends to reduce the efficiency of the oligomerization catalyst. In a preferred embodiment, any phosphorous-containing impurities are removed from the lower olefin feed using a sorbent. Phosphorous may also may be removed from the selectively branched olefin product using a sorbent.

The sorbent of the present invention may be substantially any suitable sorbent capable of sorbing phosphorus-containing impurities, preferably neutral and acidic sorbents, most preferably acidic sorbents. Preferred sorbents comprise acidic ion exchange resins, metals and metal oxides on a suitable support. Preferred metals are transition metals, including but not necessarily limited to those selected from Groups 3–12 of the Periodic Table of the Elements. When the Periodic Table of the Elements is referred to herein, the source of the Periodic Table is: F. Cotton et al. *Advanced Inorganic Chemistry* (5th Ed. 1988). Suitable metals include, but are not necessarily limited to Sc, Ti, V, Cr, Fe, Co, Ni, Cu, Zn, Zr, Nb, Mn, Ag and combinations thereof. Preferred metals are Fe, Co, Ni, Mn, Ag and Cu. In a preferred embodiment, the metal is silver or copper, preferably in the form of oxides. The sorbent suitably comprises from about 0.1 wt. % to about 50 wt. % of the metal oxide of the foregoing metals, preferably copper. Preferably, the sorbent comprises from about 1 wt. % to about 50 wt. %, more preferably from about 5 wt. % to about 35 wt. %, and most preferably from about 8 wt. % to about 20 wt. % of the metal oxide.

The metal oxide resides on a suitable support material. Although the surface area of the support is not a critical feature, the surface area preferably is at least about 10 m$^2$/g in order to provide sufficient contact between the sorbent and the olefin stream. In a preferred embodiment, the support has a surface area of from about 100 m$^2$/g to about 900 m$^2$/g. Acidic supports are more advantageous than basic supports. Suitable support materials are acidic or neutral, most preferably acidic. Suitable support materials include, but are not necessarily limited to alumina, silica, molecular sieves, such as zeolites, activated carbon, aluminosilicate clays, amorphous silicoaluminas, and the like. Where the support material surface is porous, the pores preferably are sufficiently large to permit entry of bulky phosphorus containing compounds in the feed. A most preferred support material for copper is an acidic or neutral alumina. A most preferred support material for silver is X-zeolite. A commercially available sorbent that is suitable for use in the present invention is SELEXSORB AS™, which is commercially available from Alcoa Industrial Chemicals.

It is preferred for the particles of supported sorbent to be as small as possible; however, if the size of the particles is too small, the pressure drop through the bed becomes too large. Very small particles also are difficult to retain in the sorbent bed. SELEXSORB AS™ is purchased in the form of 1/8 inch spheres, and may be used in the process as purchased. However, spheres are not the most efficient particle shape for purposes of maximizing particle surface to volume ratio. Because of this, if SELEXSORB AS™ is used as the sorbent, it is preferred to grind or otherwise reduce the 1/8 inch spheres into the smallest particles possible without inducing an undue pressure drop or loss of sorbent from the sorbent bed. The particles may have substantially any form, including but not necessarily limited to spherical form, tablet form, cylindrical form, multi-lobed cylindrical forms, and their corresponding hollow counterparts. In a preferred embodiment, the particles have a diameter of from about 50 mesh to about 6 mm, preferably about 0.8 mm (1/32 inch) to about 1.6 mm (1/16 inch), most preferably about 0.8 mm. The length of the particles is not critical, with suitable lengths including, but not necessarily limited to less than about 10 mm, preferably from about 3 mm to about 5 mm.

In a preferred embodiment, the support material is an alumina extrudate which is extruded as a paste using an acidic or neutral alumina powder. The "paste" is extruded or otherwise molded in to a multi-lobed cylindrical form. The resulting material preferably is dried at temperatures of at least about 100° C. and calcined at about 500° C. or more in the presence of flowing air in a muffle furnace or purged high temperature air drier or rotary calciner. The copper oxide may be deposited onto the support using any suitable technique, including but not necessarily limited to ion exchange, co-mulling, or impregnation. A preferred technique is pore volume impregnation using a solution of a copper salt, such as copper nitrate, copper carbonate, or other suitable salts. Although the following illustration uses a copper nitrate solution, the use of other Cu salt solutions may produce a more uniform Cu loading. Copper nitrate is very soluble in water, and tends to wick out of the pores during drying. The result may be more CuO on the outside of the pellets, although smaller pellets are less prone to this effect.

Persons of ordinary skill in the art have the knowledge required to calculate how to incorporate a given wt% of CuO or other material onto a sorbent using the foregoing techniques. For example, where 100 g of an alumina has a water pore volume of 83 ml, a 100 g of sorbent containing 9 wt. % CuO is produced by impregnating 91 g of anhydrous alumina with a copper nitrate solution. The impregnating solution is prepared by dissolving 26.3 g of $Cu(NO_3)_2 \cdot 2.5$ $H_2O$ into enough water to yield a total of 80 ml. The alumina is impregnated by dropwise addition of the copper nitrate solution.

In the case of Cu salts, the color of the filled pellets is light blue and the unfilled pellets remain white. The sorbent is dried in an oven at a temperature sufficient to boil water from the pores without fracturing the sorbent—about 121° C. (250° F.)—for from about 4 to about 8 hours. Then, the temperature is ramped to about 482° C. (900° F.) to decompose the nitrate salt to CuO on the support. Prior to use, the sorbent is stripped with nitrogen in order to avoid contaminating the olefin feed with oxygen.

In another preferred embodiment, suitable sorbents comprise neutral and acidic sorbents, most preferably acidic sorbents. Suitable neutral sorbents include neutral aluminas, activated carbons, and metal impregnated activated carbons, such as BARNEBEY CE, a silver impregnated carbon available from Barnebey & Sutcliffe. Suitable acidic sorbents include, but are not necessarily limited to acidic ion exchange resins and acidic aluminas. Suitable commercially available aluminas include, but are not necessarily limited to acidic and neutral activated aluminas, such as those available from Aldrich Chemical Co. and Selecto Scientific Co. Also suitable are the modified aluminas, such as SELEXSORB CDO 200, SELEXSORB CDX, AND SELEXSORB CD. These aluminas are modified to improve the sorption of polar organics, and are commercially available from Alcoa Industrial Chemicals. Also suitable are acidic ion exchange resins, such as AMBERLYST 15 RESIN, available from Rohm & Haas Chemical Co.

In a preferred embodiment, the sorbent is an acidic ion exchange resin, most preferably AMBERLYST 15, which generally may be used as received from the supplier.

In another preferred embodiment, the sorbent is an alumina extrudate which is extruded as a paste using an acidic or neutral alumina powder. The "paste" is extruded or otherwise molded into a multi-bed cylindrical form. The resulting material preferably is dried at temperatures of at least about 100° C. and calcined at about 500° C. or more in the presence of flowing air in a muffle furnace or purged high temperature air drier or rotary calciner.

Preferably, the olefin feedstock is contacted in the liquid phase in a reaction zone with the sorbent of the present invention at effective process conditions to reduce the content of phosphorous-containing compounds in the feedstock, i.e., an effective temperature, pressure, and LHSV (Liquid Hourly Space Velocity). A preferred embodiment of a reactor system for the process is an upflow or downflow fixed bed reactor. An upflow reactor is preferred for better wetting of the sorbent bed. The temperature employed may vary. Although not limited to a particular temperature, best results will be obtained if the process is conducted at temperatures of from about 0° C. to about 100° C., preferably from about 10° C. to about 50° C. The pressures may vary over a range including but not limited to autogeneous pressures and pressures in the range of from about 0.01 MPa to about 50 MPa. A preferred pressure is in the range of from about 0.1 MPa to about 10 MPa. Pressures outside of the stated ranges may be used and are not excluded from the scope of the invention.

The feedstock may flow at a wide range of liquid hourly space velocities (LHSV), defined as liquid feed per hour per volume of sorbent. The LHSV is calculated as follows:

$$\frac{\text{Volume of olefin containing feed}}{\text{Volume of sorbent}} \times \frac{1}{\text{hr}} = LHSV$$

The lower the LHSV, the greater will be the reduction in content of phosphorus-containing compounds in the feedstock. The LHSV generally is from about 0.01 $hr^{-1}$ to about 10 $hr^{-1}$, preferably from about 0.1 $hr^{-1}$ to about 1 $hr^{-1}$.

The process is continued for a period of time sufficient to achieve a desired reduction in the content of phosphorus-containing compounds in the olefin stream. The content of phosphorus-containing compounds preferably is reduced to about 1 ppm or less, most preferably to about 0.1 ppm or less. The time for which the sorbent is effective in reducing the phosphorus content of the feed may vary from seconds to a number of months. The time is largely determined by the reaction temperature, the pressure, the sorbent selected, the liquid hourly space velocity, the initial amount of phosphorous in the feed and the desired reduction in content of phosphorus containing compounds.

At some point, the sorbent becomes saturated with phosphorous compounds, and must be regenerated. SELEXSORB AS™ has a sorptive capacity of about 0.6 g of phosphorus per gram of sorbent. A copper oxide sorbent may be regenerated by exposing the sorbent to an oxygen-containing atmosphere at a temperature of from about 200° C. to about 600° C., preferably from about 450° C. to about 600° C. Suitable oxygen containing atmospheres include, but are not necessarily limited to air, oxygen gas, and a combination of oxygen gas with nitrogen gas. A preferred gas is a commercially available combination comprising about 1% oxygen, with the remainder being nitrogen. After exposure to these increased temperatures for a period of time of from about 0.5 hour to about 100 hours, the bed is cooled to at least about 100° C., and preferably to about 25° C., or ambient temperature, in order to avoid overheating upon reuse. The cooled bed is purged with nitrogen or air before reuse in the process. At least 10 regeneration cycles under these conditions have been shown to produce no loss in sorbent capacity. Some slight loss in sorbent capacity was seen beginning after about 10 regeneration cycles.

Diene Removal

Typical olefin feedstocks comprise dienes that tend to lower the efficiency of oligomerization and hydroformylation catalysts. The sorbents of the present invention are useful for sorbing dienes from the feedstream, both before and after the olefin feedstock contacts the oligomerization catalyst. In a preferred embodiment, the sorbent of the present invention may be used to sorb dienes from initial lower olefin streams before contact with the oligomerization catalyst in addition to lowering the phosphorus content of the olefin stream. Substantially all of the sorbents listed herein may be used for this purpose. A preferred sorbent for removing dienes is alumina.

In a preferred embodiment, dienes present in the selectively branched olefins formed during oligomerization are selectively hydrogenated in the presence of a suitable catalyst. In order to accomplish the required selective hydrogenation of dienes to olefins, one of the unsaturated carbon-carbon bonds in the dienes is selectively hydrogenated, leaving a mono-olefin. The invention accomplishes this selective hydrogenation by feeding the lower olefins at a relatively slow (trickle flow) rate to a known, selective hydrogenation catalyst in the presence of a reduced hydrogen content reaction gas.

Any suitable low activity/high selectivity (or "mild") hydrogenation catalyst may be used. Suitable catalysts typically comprise, on a suitable support, a metal selected from Groups 9, 10, or 11 of the Periodic Table of the Elements, F. Cotton et al. *Advanced Inorganic Chemistry* (Fifth Ed. 1998). Preferred metals for use as a catalytic agent in the present process are Co, Ni, Pd, and Pt, most preferably palladium, either alone or alloyed with Ag, Cu, Co, and combinations thereof. The reactivity of the catalyst may be reduced to achieve selectivity by using less of a more active metal on the support or by using a less reactive metal. Where palladium is used as the catalytic agent, the concentration of palladium on a support is from about 0.05 to about 0.5 wt. %, preferably about 0.05 to about 0.2 wt. %.

Examples of suitable supports for the catalytic metal include, but are not necessarily limited to aluminas, silicas, molecular sieves, activated carbon, aluminosilicate clays, and amorphous silicoaluminas, preferably alumna, silica and carbon. Most preferred support materials are alumina and silica. Preferred supports have up to about 15 $m^2/g$ surface area, and preferably have from about 2 to about 5 $m^2/g$ surface area. A most preferred catalyst for use in the present invention comprises palladium on an alumina support.

The catalyst may or may not be modified using a suitable promotor, such as chromium, barium, or lanthanium. A preferred promoter is chromium at a preferred concentration of from about 0.05 to about 0.2 wt. %, preferably about 0.05 wt. %. Where chromium is used as a promoter, other suitable additives which may be used at from about 0.05 to 0.25 wt %, preferably about 0.05 wt %, include, but are not necessarily limited to Ba, La, Dy, Ce, Nb, or Sm, preferably Ba or La. A preferred commercially available catalyst is K-8327, a palladium on aluminum catalyst available from W.C. Heraeus GmbH, Catalyst Department PKT, Heraeusstrasse 12-1, D-63450 Hanau, Germany.

The catalysts preferably are used in a fixed bed trickle flow reaction mode. Persons of ordinary skill in the art would expect that a relatively long exposure time between the lower olefins and the catalyst in a trickle flow mode would result in more hydrogenation and an undesirably high production of paraffins in the product. The longer the lower olefins are exposed to the catalyst, the more selective the process is to the production of olefins. This is particularly true at a low gas flow and when the level of hydrogen in the reaction gas is limited, preferably to from about 2 to about 6 vol. %, with the remainder being an inert gas, preferably nitrogen. In other words, the longer the exposure to the catalyst and to a reaction gas having a limited hydrogen content, the higher the conversion of dienes, and the lower the yield of paraffins.

The reaction conditions are relatively mild. The lower olefins preferably are fed to the fixed bed at a liquid hourly space velocity (LHSV) of about 1.0 or less, most preferably about 0.5. The reaction pressure may be ambient, but preferably is maintained relatively low, from about 20 to about 200 psig, most preferably about 30 psig. The reaction temperature also preferably is relatively low, from about 0° C. (32° F.) to about 100° C. (212° F.), preferably from about 26° C. (80° F.) to about 49° C. (120° F.), most preferably about 38° C. (100.4° F.).

Hydroformylation

Hydroformylation is a term used in the art to denote the reaction of an olefin with CO and $H_2$ to produce an aldehyde/alcohol which has one more carbon atom than the reactant olefin. Frequently, the term hydroformylation is used to cover the aldehyde and the reduction to the alcohol step in total, i.e., hydroformylation refers to the production of alcohols from olefins via carbonylation and an aldehyde reduction process. As used herein, hydroformylation refers to the ultimate production of alcohols.

Illustrative hydroformylation catalysts include, but are not necessarily limited to, cobalt hydrocarbonyl catalysts and metal-phosphine ligands comprising metals including, but not necessarily limited to palladium, cobalt, and rhodium. The choice of catalysts determines the various reaction conditions imposed, including whether diene removal is advisable. Certain catalysts are not as susceptible to diene poisoning as others. In a preferred embodiment, diene removal is used in conjunction with palladium based catalysts, including, but not necessarily limited to palladium—phosphine ligand catalysts. One of ordinary skill in the art, by referring to any of the well-known literature on oxo alcohols, can readily determine the conditions of temperature and pressure that will be needed to hydroformylate the olefins. An example in addition to U.S. Pat. No. 5,849,960 is EP 0 903 333 A1, incorporated herein by reference.

The oligomerized, selectively branched olefins of the present invention have a variety of uses, including but not necessarily limited to uses in pulp processing, drilling fluids, and machine or metal working. In a preferred embodiment, the oligomerized selectively branched olefins are converted to any of a broad range of surfactants, including nonionic, anionic, cationic, and amphoteric surfactants, with a degree of branching of at least 1.0. The selectively branched olefins serve as a surfactant intermediate. Specifically, the selectively branched olefins serve as the hydrophobic moiety of the surfactant molecule, while the moiety added to the olefin during the conversion process serves as the hydrophile.

The invention will be better understood with reference to the following examples, which are illustrative only and should not be construed to limit the invention to a particular embodiment.

EXAMPLE I

A glass column with an inner diameter of 50 mm was packed with 3.2 mm Selexsorb AS spheres obtained from Alcoa Company of America to produce a bed 400 mm in length. A 2 L mixture of primarily $C_6$–$C_8$ NEODENE® linear, alpha and internal olefins was obtained from Shell Chemical Company. This mixture contained less than 5% wt. of $C_4$, $C_5$, $C_9$ and $C_{10}$ olefin. This mixture was passed through the packed bed of Selexsorb AS spheres at a weight hourly space velocity of 0.01 per hour and the liquid effluent was collected in a container purged with nitrogen. The phosphorus content of the $C_6$–$C_8$ NEODENE® linear, alpha and internal olefins was reduced from 4 ppm to less than 0.1 ppm in the process.

EXAMPLE II

A glass column with an inner diameter of 50 mm was packed with 3.2 mm Selexsorb AS spheres obtained from Alcoa Company of America to produce a bed 400 mm in length. A mixture of 1800 g of NEODENE6® alpha olefin and 2400 g of NEODENE8® alpha olefin was prepared using linear, alpha olefins obtained from Shell Chemical Company. This mixture contained less than 4 wt. % $C_4$ and $C_{10}$ olefins. This mixture was passed through the packed bed of Selexsorb AS spheres at a weight hourly space velocity of 0.01 per hour and the liquid efflsuent was collected in a container purged with nitrogen. The phosphorus content of the $C_6$–$C_8$ NEODENE® linear, alpha olefins was reduced from 8 ppm to less than 0.1 ppm in the process.

EXAMPLE III

A flask was charged with 2268.7 g of a $C_6$–$C_8$ internal olefins having some 4, 5, 9, and 10 carbon olefins, and distilled using an 11 plate Oldershaw distillation column with a swinging bucket reflux splitter condenser, a dry ice chilled trap, and a nitrogen blanket. After about 37 hours of distillation, those cuts distilling up to 138° C. in the pot and 125° C. at the head were collected for a total amount of about 1200 g. These cuts represent the light ends of the olefin, $C_{4-8}$.

The 1200 g of the $C_{4-8}$ olefin feed was dimerized by the following method.

The 1200 g of the olefin was poured into a 5 L round bottom flask equipped with a condenser, a dry ice condenser, a thermocouple, a water bath, and a nitrogen blanket.

About 19.74 g of dried nickel hexafluoroacetoacetyl acetonate (nickel catalyst) and 53.76 g of an 11/89 wt. % solution of diethylaluminum ethoxide in cyclohexane (aluminum solution) were added sequentially and stirred into the olefin. The reaction mixture was heated up to 35° C. for 6 and ½ hours, after which 14.38 g of the aluminum solution were added, heated up to 37° C. for an additional 2 hours, after which 4.0 g of the nickel catalyst and 13.75 g of the aluminum solution were added, heated up to 35° C. to 37° C. for about another 10 hours, after which 15.55 g of the aluminum solution were added followed by heating for another 4 hours, after which 4 g of the nickel catalyst and 14.4 g of the aluminum solution were added, followed by heating for another 5 hours, after which 21.0 g of the aluminum solution and 5.0 g of the nickel catalyst were added, followed by heating for another 3 hours, after which 4.18 g of the nickel catalyst and 20.1 g of the aluminum solution were added.

Subsequently, the reaction product in the flask was quenched with 100 g of citric acid and about 22 g of a sodium bicarbonate solution per quart of water, and filtered.

The dimerized $C_{4-8}$ olefin was then subjected to further distillation to obtain cuts having predominantly $C_{13-14}$ olefins. The distillation was conducted as above, except with a 10 plate Oddershaw column, and those cuts distilling at 169° C. to 194° C. in the pot and 129° C. to 155° C. at the head, at 47 to 48 mmHg vacuum, were collected, for a total of 188.05 g.

EXAMPLE IV

Example III was repeated with the exception that the olefin mixture was passed over the Selexsorb AS as described above in Example I. A 6% greater yield of primarily mono-branched $C_{13}$ and $C_{14}$ olefins was obtained after distillation, (199.30 g of product) as compared to 188.05 g obtained in Example III. 150 g of the primarily mono-branched $C_{13}$ and $C_{14}$ olefin products obtained were subjected to hydroformylation in a 500 ml autoclave, using the modified oxo process. The 150 g of the dimerized olefin were reacted with hydrogen and carbon monoxide at a $H_2$/CO ratio of 2, in the presence of a phosphine modified cobalt catalyst and potassium hydroxide in ethanol at a temperature of up to about 180° C., a stirring speed of 1250 rpm, and a pressure of about 1000 psig, for about 20 hours. After completion of the reaction, the product was cooled to 60° C.

The hydroformylated dimerized alcohols were subjected to further flash volatilization to separate out any unconverted olefin and paraffins. Those cuts distilling at 182° C. to 250° C. in the pot and 99° C. to 112° C. at the head were collected, and neutralized with sodium borohydride. The distillate cuts, totaling 300 ml, were added to a round bottom flask, stirred and heated to 50° C., to which 0.6 g of the sodium borohydride were added and reacted for about 2 hours, after which 0.6 g of the sodium borohydride were added and reacted for another 1.5 hours at 75° C. –80° C., and then reacted for another 2 and ½ hours at 98° C. –100° C. The solution was left to cool, transferred to a 500 ml flask, washed by shaking with 70° C. deionized water under ventilation, let stand, to which was added 20 ml of ethyl ether, shaken, and separated. The water phase was drained and the process repeated another two times using ethyl ether. After washing, about 10 g of sodium sulfate was added to the alcohol, was shaken, and then allowed stand. The product was filtered, the liquid transferred to a 250 ml flask, and then subjected to further distillation to rid the solution of the light ends. The distillates obtained up to 102° C. in the pot and 163° C. at the head were discarded, and 85 ml of the contents in the pot were recovered. These contents were mono-branched $C_{12-16}$ alcohols, having about 42% $C_{14}$, 45% $C_{15}$ and 7% $C_{16}$ mono-branched alcohols as determined by GCMS, and were subjected to analytical testing and further reaction for making the sulfates.

EXAMPLE V

In this example, a mixture of 600 g NEODENE® 6 alpha.-olefin, a $C_6$ olefin, and 800 g of NEODENE® 8 alpha.-olefin, a $C_8$ olefin, containing 5.32 g of ethylaluminum dichloride, were added to a 5 L flask. The same procedure as used in Example I was followed with the following differences. A solution of 7.9 g of the nickel 2-ethylhexanoate-trifluoroacetate in 6.35 g of cyclohexane (the nickel solution) was added and heated. The flask was maintained at from 33° C. to 38° C. throughout the course of the reaction. Another 7.6 ml of the aluminum solution as prepared in example 2 and 5 ml of the nickel solution were injected into the reaction flask after about 8 hours of heating.

About 1.5 L of the sodium citrate neutralizing solution was used to neutralize the dimerized olefins, separated, and again repeated. The dimerized product was distilled, with the cuts distilling at 149° C. to 160° C. in the pot and 137° C. to 148° C. at the head, at 60 mmHg, 120° C. to 133° C. in the pot and 110° C. to 122° C. at the head at 9 mmHg, and 127° C. to 149° C. in the pot and 118° C. to 145° C. at the head at 10 mmHg being collected for a total of 786.4 g.

730 g of these dimerized olefins were hydroformylated in a 1 gallon autoclave, reacted at temperatures up to about 240° C. at pressures up to 1145 psig.

809 g of the hydroformylated olefins were treated with 6.5 g of sodium borohydride, as above, followed by another addition of 6.5 g of sodium borohydride and heating, and a third addition of 4.95 g followed by 6 hours of heating at up to 99° C.

The treated hydroformylated olefins were washed as in Example III, filtered, and distilled with those cuts distilling at 152° C. to 181° C. in the pot and 137° C. to 172° C. at the head at 6 mmHg being collected for a total of 495 g of $C_{13}$, $C_{15}$, and $C_{17}$ mono-branched alcohols. The sample was analytically tested and sulfated as described below.

EXAMPLE VI

The experiment in Example V was repeated with the exception that the olefin mixture was treated in the manner described in Example II above. A 7% greater yield of primarily mono-branched $C_{12}$ and $C_{16}$ olefins was obtained after distillation, (841.4 g of product). 730 g of the primarily mono-branched $C_{12}$, $C_{14}$ and $C_{16}$ olefin products obtained were hydroformylated as in Example V. After distillation to remove lights, a total of 499 g of the $C_{13}$–$C_{17}$ hydroformylated product was recovered. The product contained primarily mono-branched alcohols.

EXAMPLE VII

A catalyst was prepared using an ammonium-ferrierite having a molar silica to alumina ratio of 62:1, a surface area of 369 m²/g (P/Po=0.03), a soda content of 480 ppm and n-hexane sorption capacity of 7.3 g per 100 g of zeolite was used as the starting zeolite. The catalyst components were mulled using a Lancaster mix muller. The mulled catalyst material was extruded using a 2.25 inch Bonnot pin barrel extruder.

The catalyst was prepared using 1 wt. % acetic acid and 1 wt. % citric acid. The Lancaster mix muller was loaded with 645 g of ammonium-ferrierite (5.4% LOI) and 91 g of CATAPAL D® alumina (LOI of 25.7%) purchased from Vista Chemical of Houston, Tex. The alumina was blended with the ferrierite for 5 minutes during which time 152 ml of de-ionized water was added. A mixture of 6.8 g glacial acetic acid, 7.0 g of citric acid and 152 ml of de-ionized water was added slowly to the muller in order to peptize the alumina. The mixture was mulled for 10 minutes. 0.20 g of tetraammine palladium nitrate in 153 g of de-ionized water were then added slowly as the mixture was mulled for an additional period of 5 minutes. Ten grams of METHOCEL F4M® hydroxypropyl methylcellulose was added and the zeolite/alumina mixture was mulled for 15 additional minutes. The 90:10 zeolite/alumina mixture was transferred to the 2.25 inch Bonnot extruder and extruded using a die plate with 1/16" holes.

The moist extrudates were tray dried in an oven heated to 150° C. 2 hours, and then increased to 175° C. for 4 hours. After drying, the extrudates were broken manually. The extrudates were calcined in flowing air at 500° C. for two hours.

A 500 mL autoclave was charged under nitrogen with 20 g of the zeolitic catalyst and 140 g of the primarily linear $C_{6-8}$ alpha olefin mixture obtained above in Example II. The autoclave was closed and stirring was begun. The autoclave was heated to 200° C. and then held at this temperature for a period of 2 hours. The slurry was allowed to cool and then was filtered to remove the zeolitic catalyst from the olefinic products. After distillation to remove the lighter products, a total of 78 g of $C_{10}$ to $C_{18}$ olefins were obtained. More than 90% of these olefins were found to be mono-branched.

EXAMPLE VIII

A glass column with an inner diameter of 50 mm was packed with 150 mesh neutral, activated aluminum oxide (Brockmann I) obtained from Aldrich Chemical Company to produce a bed 400 mm in length. 20 L of a mixture of primarily linear $C_{14-19}$ olefins, obtained from and commercially available from Shell Chemical Company, was passed through the packed bed at a weight hourly space velocity of 0.5 per hour and the liquid effluent was collected in a container purged with nitrogen. The diene content of the mixed $C_{14}$–$C_{19}$ olefins was reduced from 270 ppm to 20 ppm in the process.

EXAMPLE IX

A glass column with an inner diameter of 50 mm was packed with 150 mesh neutral, activated aluminum oxide (Brockmann I) obtained from Aldrich Chemical Company to produce a bed 400 mm in length. Olefins were prepared using the method of Example V and distilled to obtain a mixture of $C_{14}$–$C_{18}$ selectively branched olefins. The selectively branched olefins were passed through the packed bed at a weight hourly space velocity of 0.1 per hour and the liquid effluent was collected in a container purged with nitrogen. The diene content of the selectively branched olefins was reduced from 240 ppm to 24 ppm in the process.

As can be seen from the data, $C_6$–$C_{10}$ linear olefins can be converted in good yields into heavier olefins that are primarily mono-branched. These mono-branched olefins can be hydroformylated in good yield into mono-branched alcohols which are useful in a number of important commercial applications. The removal of basic phosphorus compounds improves the recoverable yield of the desired products.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A process for making a selectively branched alcohol composition, comprising:

providing a lower olefin feed comprising linear olefins having at least 3 carbon atoms and comprising a concentration of an impurity comprising dienes;

contacting said branched olefins under hydrogenation conditions with a catalyst effective to selectively hydrogenate dienes to mono-olefins, thereby substantially reducing said concentration of said impurity;

contacting said lower olefin feed with an oligomerization catalyst under oligomerization conditions, said oligomerization catalyst being effective to oligomerize said linear olefins to produce selectively branched olefins having up to about 36 carbon atoms; and converting said selectively branched olefins to said selectively branched alcohol composition.

2. The process of claim 1, wherein a majority of said selectively branched olefins are mono-branched olefins.

3. A process for making a selectively branched alcohol composition, comprising:

providing a lower olefin feed comprising linear olefins having at least 3 carbon atoms;

contacting said lower olefin feed with an oligomerization catalyst under oligomerization conditions, said catalyst being effective to oligomerize said linear olefins to produce selectively branched olefins having up to about 36 carbon atoms, wherein said selectively branched olefins comprise a concentration of dienes;

contacting said selectively branched olefins under hydrogenation conditions with a catalyst effective to selectively hydrogenate dienes to mono-olefins, thereby reducing said concentration of said dienes; and converting said selectively branched olefins to said selectively branched alcohol composition.

4. The process of claim 3, wherein said oligomerization catalyst is selected from the group consisting of molecular sieves and homogeneous dimerization catalysts.

5. The process of claim 3 wherein said oligomerization catalyst comprises a zeolite having a ferrierite isotopic structure.

6. The process of claim 4, wherein said homogeneous dimerization catalyst is selected from the group consisting of a combination of a nickel carboxylate and an alkyl aluminum halide and a combination of a nickel chelate and an alkyl aluminum alkoxide.

7. The process of claim 3, wherein said branched olefin comprises from about 9 to about 33 carbon atoms.

8. The process of claim 3 further comprising contacting said lower olefin feed with an amount of sorbent effective to remove dienes from said lower olefin feed.

9. The process of claim 3, wherein said lower olefin feed comprises a concentration of dienes, further comprising reducing said concentration of dienes in said lower olefin feed.

10. A process for making a selectively branched alcohol composition, comprising:

providing a lower olefin feed comprising linear olefins having at least 3 carbon atoms and a concentration of phosphorous-containing compounds;

reducing said concentration of said phosphorous-containing compounds;

contacting said lower olefin feed with an oligomerization catalyst under oligomerization conditions, said catalyst being effective to oligomerize said linear olefins to produce selectively branched olefins having up to about 36 carbon atoms and a concentration of dienes;

contacting said selectively branched olefins under hydrogenation conditions with a catalyst effective to hydrogenate dienes, thereby reducing said concentration of said dienes; and converting said selectively branched olefins to said selectively branched alcohol composition.

11. The process of claim 10, wherein said phosphorous reduction comprises contacting said lower olefin feed with a sorbent selected from the group consisting of an acidic ion exchange resin, an acidic zeolite, an acidic alumina, a neutral alumina, an activated carbon, and a metal under conditions and for a time effective to permit said sorbent to reduce said content of phosphorus-containing compounds and to produce a purified lower olefin feed.

12. A process for making a selectively branched alcohol composition, comprising:

providing a lower olefin feed comprising linear olefins having at least 3 carbon atoms and a concentration of phosphorous-containing compounds;

contacting said lower olefin feed with a sorbent comprising a metal selected from the group consisting of Sc, V, Cr, Fe, Co, Ni, Cu, Zn, Nb, Mn, Ag and combinations thereof on a support in an amount and under conditions effective to substantially reduce said concentration of said phosphorous-containing compounds in said lower olefin feed;

contacting said lower olefin feed with an oligomerization catalyst under oligomerization conditions, said catalyst being effective to oligomerize said linear olefins to produce selectively branched olefins having up to about 36 carbon atoms; and converting said selectively branched olefins to said selectively branched alcohol composition.

13. The process of claim 12 wherein said sorbent comprises a metal selected from the group consisting of Fe, Co, Ni, Mn, Ag and Cu.

14. The process of claim 12 wherein said sorbent comprises a metal selected from the group consisting of silver and copper.

15. The process of claim 12 wherein said sorbent comprises an oxide of a metal selected from the group consisting of silver and copper.

16. A process for making a selectively branched alcohol composition, comprising:

providing a lower olefin feed comprising linear olefins having at least 3 carbon atoms and a concentration of phosphorous-containing compounds;

contacting said lower olefin feed with a sorbent comprising copper oxide on a support in an amount and under conditions effective to substantially reduce said concentration of said phosphorous-containing compounds in said lower olefin feed;

contacting said lower olefin feed with an oligomerization catalyst under oligomerization conditions, said catalyst being effective to oligomerize said linear olefins to produce selectively branched olefins having up to about 36 carbon atoms; and converting said selectively branched olefins to said selectively branched alcohol composition.

17. The method of claim 12 wherein said support is acidic.

18. The method of claim 12 wherein said support is selected from the group consisting of alumina, silica, molecular sieves, activated carbon, aluminosilicate clays, and amorphous silicoaluminas.

19. The process of claim 16 wherein said support is selected from the group consisting of acidic and neutral alumina.

20. A process for making a selectively branched alcohol composition, comprising:

providing a lower olefin feed comprising linear olefins having at least 3 carbon atoms and a concentration of phosphorous-containing compounds;

contacting said lower olefin feed with a sorbent comprising a transition metal on a support in an amount and under conditions effective to reduce said concentration of said phosphorous-containing compounds in said lower olefin feed to about 0.1 ppm or less;

contacting said lower olefin feed with an oligomerization catalyst under oligomerization conditions, said catalyst being effective to oligomerize said linear olefins to produce selectively branched olefins having up to about 36 carbon atoms; and converting said selectively branched olefins to said selectively branched alcohol composition.

21. The process of claim 20 wherein said converting comprises contacting said branched olefin with a hydroformylation catalyst.

22. The process of claim 20 wherein said oligomerization catalyst is selected from the group consisting of molecular sieves and homogeneous dimerization catalysts.

23. The process of claim 22, wherein said oligomerization catalyst comprises a zeolite having a ferrierite isotopic structure.

24. The process of claim 22, wherein said homogeneous dimerization catalyst is selected from the group consisting of a combination of a nickel carboxylate and an alkyl aluminum halide and a combination of a nickel chelate and an alkyl aluminum alkoxide.

25. The process of claim 20 wherein said branched olefin comprises from about 9 to about 33 carbon atoms.

26. The process of claim 21 wherein a portion of said selectively branched olefins are mono-branched olefins.

27. The process of claim 20 wherein said selectively branched olefins comprise a concentration of phosphorous compounds, further comprising reducing said concentration of phosphorous compounds in said selectively branched olefins.

28. The process of claim 20 wherein said selectively branched olefins comprise a concentration of dienes, further comprising reducing said concentration of said dienes in said selectively branched olefins.

29. The process of claim 20 wherein said lower olefin feed comprises a concentration of dienes, further comprising reducing said concentration of dienes in said lower olefin feed.

30. A process for making a selectively branched alcohol composition, comprising:

providing a lower olefin feed comprising linear olefins having at least 3 carbon atoms and a concentration of phosphorous-containing compounds;

contacting said lower olefin feed with a sorbent comprising a transition metal on a support in an amount and under conditions effective to reduce said concentration of said phosphorous-containing compounds in said lower olefin feed, producing a purified lower olefin feed;

contacting said purified lower olefin feed with an oligomerization catalyst under oligomerization conditions, said oligomerization catalyst being effective to oligomerize said linear olefins to produce selectively branched olefins having up to about 36 carbon atoms, said selectively branched olefins comprising a concentration of dienes;

reducing said concentration of said dienes in said selectively branched olefins by about 90% or more to produce purified selectively branched olefins; and converting said purified selectively branched olefins to said selectively branched alcohol composition.

31. A process for making a selectively branched alcohol composition, comprising:

providing a lower olefin feed comprising linear olefins having at least 3 carbon atoms, said lower olefin feed comprises a concentration of dienes and a concentration of phosphorous-containing compounds;

contacting said lower olefin feed with a sorbent comprising a transition metal on a support in an amount and under conditions effective to reduce said concentration of said phosphorous-containing compounds in said lower olefin feed;

reducing said concentration of dienes in said lower olefin feed by about 90% or more, producing a purified lower olefin feed;

contacting said purified lower olefin feed with an oligomerization catalyst under oligomerization conditions, said catalyst being effective to oligomerize said linear olefins to produce selectively branched olefins having up to about 36 carbon atoms; and converting said selectively branched olefins to said selectively branched alcohol composition.

32. The process of claim 3 wherein said reducing said concentration of dienes in said selectively branched olefins comprises a reduction of about 90% or more.

33. The process of claim 8 wherein said reducing said concentration of dienes in said selectively branched olefins comprises a reduction of about 90% or more.

34. The process of claim 9 wherein said reducing said concentration of dienes in said lower olefin feed comprises a reduction of about 90% or more.

35. A process for making a selectively branched alcohol composition, comprising:

contacting an oligomerization catalyst under oligomerization conditions with a lower olefin feed comprising linear olefins having at least 3 carbon atoms, said oligomerization catalyst being effective to oligomerize said linear olefins to produce selectively branched olefins having up to about 36 carbon atoms, wherein said selectively branched olefins comprise a concentration phosphorous containing compounds;

contacting said selectively branched olefins with a sorbent comprising a transition metal for a time effective to permit said sorbent to reduce said content of phosphorus-containing compounds and to produce a purified lower olefin feed; and converting said selectively branched olefins to said selectively branched alcohol composition.

36. The process of claim 35, wherein said selectively branched olefins further comprise a concentration of dienes and said sorbent reduces said concentration of dienes.

37. The process of claim 35 wherein said sorbent comprises a metal selected from the group consisting of Sc, Ti, V, Cr, Fe, Co, Ni, Cu, Zn, Zr, Nb, Mn, Ag and combinations thereof.

38. The process of claim 35 wherein said sorbent comprises a metal selected from the group consisting of Fe, Co, Ni, Mn, Ag and Cu.

39. The process of claim 35 wherein said sorbent comprises a metal selected from the group consisting of silver and copper.

40. The process of claim 35 wherein sorbent comprises an oxide of a metal selected from the group consisting of silver and copper.

41. A process for making a selectively branched alcohol composition, comprising:

contacting an oligomerization catalyst under oligomerization conditions with a lower olefin feed comprising linear olefins having at least 3 carbon atoms, said oligomerization catalyst being effective to oligomerize said linear olefins to produce selectively branched olefins having up to about 36 carbon atoms, wherein said selectively branched olefins comprise a concentration phosphorous containing compounds;

contacting said selectively branched olefins with a sorbent comprising copper oxide on a support under conditions and for a time effective to permit said sorbent to substantially reduce said content of phosphorus-containing compounds and to produce purified selectively branched olefins; and converting said purified selectively branched olefins to said selectively branched alcohol composition.

42. The process of claim 41 wherein said support is acidic.

43. The process of claim 41 wherein said support is selected from the group consisting of alumina, silica, molecular sieves, activated carbon, aluminosilicate clays, and amorphous silicoaluminas.

44. The process of claim 41 wherein said support is selected from the group consisting of acidic and neutral alumina.

45. The process of claim 41 wherein said concentration of phosphorous-containing compounds in said selectively branched olefins is reduced to about 1 ppm or less.

46. The method of claim 41 wherein said concentration of phosphorous-containing compounds in said selectively branched olefins is reduced to about 0.1 ppm or less.

47. The method of claim 42 wherein said concentration of phosphorous-containing compounds in said selectively branched olefins is reduced to about 1 ppm or less.

48. The method of claim 42 wherein said concentration of phosphorous-containing compounds in said selectively branched olefins is reduced to about 0.1 ppm or less.

49. The method of claim 16 wherein said conditions comprise a temperature of from about 0° C. to about 100° C.

50. The method of claim 16 wherein said conditions comprise a temperature of from about 10° C. to about 50° C.

51. The method of claim 35 wherein said conditions comprise a pressure of from about 0.1 MPa to about 10 MPa.

52. The method of claim 35 wherein said conditions comprise a liquid hourly space velocity (LHSV) of from about 0.01 hr$^{-1}$ to about 10 hr$^{-1}$.

53. The method of claim 35 wherein said conditions comprise an LHSV of from about 0.1 hr$^{-1}$ to about 1 hr$^{-1}$.

54. The method of claim 41 wherein said conditions comprise a temperature of from about 0° C. to about 100° C.

55. The process of claim 41 wherein said conditions comprise a temperature of from about 10° C. to about 50° C.

56. The process of claim 55 wherein said conditions comprise a pressure of from about 0.1 MPa to about 10 MPa.

57. The process of claim 56 wherein said conditions comprise a liquid hourly space velocity (LHSV) of from about 0.0 hr$^{-1}$ to about 10 hr$^{-1}$.

58. The process of claim 56 wherein said conditions comprise an LHSV of from about 0.1 hr$^{-1}$ to about 1 hr$^{-1}$.

59. The process of claim 35 wherein said concentration of phosphorous-containing compounds in said selectively branched olefins is reduced to about 1 ppm or less.

60. The process of claim 35 wherein said concentration of phosphorous-containing compounds in said selectively branched olefins is reduced to about 0.1 ppm or less.

61. The process of claim 37 wherein said concentration of phosphorous-containing compounds in said selectively branched olefins is reduced to about 1 ppm or less.

62. The process of claim 37 wherein said concentration of phosphorous-containing compounds in said selectively branched olefins is reduced to about 0.1 ppm or less.

63. The process of claim 38 wherein said concentration of phosphorous-containing compounds in said selectively branched olefins is reduced to about 1 ppm or less.

64. The process of claim 38 wherein said concentration of phosphorous-containing compounds in said selectively branched olefins is reduced to about 0.1 ppm or less.

65. The process of claim 39 wherein said concentration of phosphorous-containing compounds in said selectively branched olefins is reduced to about 1 ppm or less.

66. The process of claim 39 wherein said concentration of phosphorous-containing compounds in said selectively branched olefins is reduced to about 0.1 ppm or less.

67. The process of claim 40 wherein said concentration of phosphorous-containing compounds in said selectively branched olefins is reduced to about 1 ppm or less.

68. The process of claim 40 wherein said concentration of phosphorous-containing compounds in said selectively branched olefins is reduced to about 0.1 ppm or less.

69. The process of claim 16 wherein said sorbent comprises particles having a diameter of about 50 mesh to about 6 mm.

70. The process of claim 16 wherein said sorbent comprises particles having a diameter of from about 0.8 mm to about 1.6 mm.

71. The process of claim 41 wherein said sorbent comprises particles having a diameter of about 50 mesh to about 6 mm.

72. The process of claim 41 wherein said sorbent comprises particles having a diameter of from about 0.8 mm to about 1.6 mm.

73. The process of claim 35 wherein said support is selected from the group consisting of acidic and neutral alumina.

74. The process of claim 12 wherein said concentration of phosphorous-containing compounds in said selectively branched olefins is reduced to about 1 ppm or less.

75. The process of claim 12 wherein said concentration of phosphorous-containing compounds in said selectively branched olefins is reduced to about 0.1 ppm or less.

76. The process of claim 12 wherein said conditions comprise a temperature of from about 0° C. to about 100° C.

77. The process of claim 12 wherein said conditions comprise a temperature of from about 10° C. to about 50° C.

78. The process of claim 12 wherein said conditions comprise a pressure of from about 0.1 MPa to about 10 MPa.

79. The process of claim 12 wherein said conditions comprise a liquid hourly space velocity (LHSV) of from about 0.01 hr$^{-1}$ to about 10 hr$^{-1}$.

80. The process of claim 12 wherein said conditions comprise an LHSV of from about 0.1 hr$^{-1}$ to about 1 hr$^{-1}$.

81. The process of claim 12 wherein said sorbent comprises particles having a diameter of about 50 mesh to about 6 mm.

82. The process of claim 12 wherein said sorbent comprises particles having a diameter of from about 0.8 mm to about 1.6 mm.

83. The process of claim 35 wherein said oligomerization catalyst is selected from the group consisting of molecular sieves and homogeneous dimerization catalysts.

84. The process of claim 35 wherein said oligomerization catalyst comprises a zeolite having a ferrierite isotopic structure.

85. The process of claim 35 wherein said homogeneous dimerization catalyst is selected from the group consisting of a combination of a nickel carboxylate and an alkyl aluminum halide and a combination of a nickel chelate and an alkyl aluminum alkoxide.

86. The process of claim 35 wherein said branched olefin comprises from about 9 to about 33 carbon atoms.

87. A process for making a selectively branched alcohol composition, comprising:
providing a lower olefin feed comprising linear olefins having at least 3 carbon atoms and a concentration of phosphorous-containing compounds;
contacting said lower olefin feed with a sorbent comprising a metal selected from the group consisting of Sc, Ti, V, Cr, Fe, Co, Ni, Cu, Zn, Zr, Nb, Mn, Ag and combinations thereof on a support in an amount and under conditions effective to substantially reduce said concentration of said phosphorous-containing compounds in said lower olefin feed;
contacting said lower olefin feed with an amount of sorbent effective to remove dienes from said lower olefin feed;
contacting said lower olefin feed with an oligomerization catalyst under oligomerization conditions, said catalyst being effective to oligomerize said linear olefins to produce selectively branched olefins having up to about 36 carbon atoms; and
converting said selectively branched olefins to said selectively branched alcohol composition.

88. A process for making a selectively branched alcohol composition, comprising:
providing a lower olefin feed comprising linear olefins having at least 3 carbon atoms, said lower olefin feed comprising a concentration of dienes and a concentration of phosphorous-containing compounds;
contacting said lower olefin feed with a sorbent comprising a metal selected from the group consisting of silver, copper, and combinations thereof on a support in an amount and under conditions effective to substantially reduce said concentration of said phosphorous-containing compounds in said lower olefin feed;
reducing said concentration of dienes in said lower olefin feed;
contacting said lower olefin feed with an oligomerization catalyst under oligomerization conditions, said catalyst being effective to oligomerize said linear olefins to produce selectively branched olefins having up to about 36 carbon atoms; and
converting said selectively branched olefins to said selectively branched alcohol composition.

89. The process of claim 35 wherein a portion of said selectively branched olefins are mono-branched olefins.

90. The process of claim 88 wherein said reducing said concentration of dienes from said lower olefin feed comprises a reduction of about 90% or more.

91. The process of claim 35 wherein said converting comprises contacting said branched olefin with a hydroformylation catalyst.

92. The process of claim 16 wherein said support is acidic.

93. The process of claim 16 wherein said support is selected from the group consisting of acidic and neutral alumina.

94. The process of claim 16 wherein said concentration of phosphorous-containing compounds in said selectively branched olefins is reduced to about 1 ppm or less.

95. The process of claim 16 wherein said concentration of phosphorous-containing compounds in said selectively branched olefins is reduced to about 0.1 ppm or less.

96. The process of claim 16 wherein said conditions comprise a pressure of from about 0.1 MPa to about 10 MPa.

97. The process of claim 16 wherein said conditions comprise a liquid hourly space velocity (LHSV) of from about $0.01$ $hr^{-1}$ to about $10$ $hr^{-1}$.

98. The process of claim 16 wherein said conditions comprise an LHSV of from about $0.1$ $hr^{-1}$ to about $1$ $hr^{-1}$.

99. The process of claim 16 wherein said oligomerization catalyst is selected from the group consisting of molecular sieves and homogeneous dimerization catalysts.

100. The process of claim 16 wherein said oligomerization catalyst comprises a zeolite having a ferrierite isotopic structure.

101. The process of claim 99 wherein said homogeneous dimerization catalyst is selected from the group consisting of a combination of a nickel carboxylate and an alkyl aluminum halide and a combination of a nickel chelate and an alkyl aluminum alkoxide.

102. The process of claim 16 wherein said branched olefin comprises from about 9 to about 33 carbon atoms.

103. A process for making a selectively branched alcohol composition, comprising:
providing a lower olefin feed comprising linear olefins having at least 3 carbon atoms and a concentration of phosphorous-containing compounds;
contacting said lower olefin feed with an amount of sorbent effective to remove dienes from said lower olefin feed;
contacting said lower olefin feed with a sorbent comprising copper oxide on a support in an amount and under conditions effective to substantially reduce said concentration of said phosphorous-containing compounds in said lower olefin feed;
contacting said lower olefin feed with an oligomerization catalyst under oligomerization conditions, said catalyst being effective to oligomerize said linear olefins to produce selectively branched olefins having up to about 36 carbon atoms; and
converting said selectively branched olefins to said selectively branched alcohol composition.

104. A process for making a selectively branched alcohol composition, comprising:
providing a lower olefin feed comprising linear olefins having at least 3 carbon atoms, said lower olefin feed comprises a concentration of dienes and a concentration of phosphorous-containing compounds;
reducing said concentration of dienes in said lower olefin feed;
contacting said lower olefin feed with a sorbent comprising copper oxide on a support in an amount and under conditions effective to substantially reduce said concentration of said phosphorous-containing compounds in said lower olefin feed;
contacting said lower olefin feed with an oligomerization catalyst under oligomerization conditions, said catalyst being effective to oligomerize said linear olefins to produce selectively branched olefins having up to about 36 carbon atoms; and converting said selectively branched olefins to said selectively branched alcohol composition.

105. The method of claim 104 wherein said reducing said concentration of dienes in said lower olefin feed comprises a reduction of about 90% or more.

106. The process of claim 16 wherein said converting comprises contacting said branched olefin with a hydroformylation catalyst.

107. The process of claim 21 wherein a portion of said selectively branched olefins are mono-branched olefins.

108. The method of claim 35 wherein said sorbent comprises particles having a diameter of about 50 mesh to about 6 mm.

109. The method of claim 35 wherein said sorbent comprises particles having a diameter of from about 0.8 mm to about 1.6 mm.

110. The method of claim 35 wherein said transition metal comprises an acidic support.

111. The method of claim 35 wherein said transition metal comprises a support comprising a material selected from the group consisting of alumina, silica, molecular sieves, activated carbon, aluminosilicate clays, and amorphous silicoaluminas.

112. The method of claim 35 wherein said transition metal comprises a support selected from the group consisting of acidic and neutral alumina.

113. The method of claim 35 wherein said conditions comprise a temperature of from about 0° C. to about 100° C.

114. The method of claim 35 wherein said conditions comprise a temperature of from about 10° C. to about 50° C.

* * * * *